United States Patent
Daikoku et al.

(10) Patent No.: US 9,551,691 B2
(45) Date of Patent: Jan. 24, 2017

(54) L-MODE GUIDED WAVE SENSOR

(75) Inventors: Koki Daikoku, Kanagawa (JP); Masato Yoshizaki, Kanagawa (JP); Shuichi Sato, Kanagawa (JP)

(73) Assignee: IHI INSPECTION AND INSTRUMENTATION CO., LTD., Tokyo (JP)

( * ) Notice: Subject to any disclaimer, the term of this patent is extended or adjusted under 35 U.S.C. 154(b) by 339 days.

(21) Appl. No.: 13/639,466

(22) PCT Filed: May 11, 2010

(86) PCT No.: PCT/JP2010/057934
§ 371 (c)(1),
(2), (4) Date: Oct. 4, 2012

(87) PCT Pub. No.: WO2011/135732
PCT Pub. Date: Nov. 3, 2011

(65) Prior Publication Data
US 2013/0036822 A1    Feb. 14, 2013

(30) Foreign Application Priority Data

Apr. 27, 2010 (JP) .................................. 2010-101817

(51) Int. Cl.
*G01N 29/24* (2006.01)
*G01N 29/04* (2006.01)

(52) U.S. Cl.
CPC ........ *G01N 29/2412* (2013.01); *G01N 29/043* (2013.01); *G01N 2291/0425* (2013.01); *G01N 2291/2634* (2013.01)

(58) Field of Classification Search
CPC .... G01N 29/00; G01N 29/04; G01N 29/2412; G01N 27/725; G01N 29/043; G01N 2291/0425; G01N 2291/2634; H01L 1/12; H04R 15/00
USPC .................................................. 73/643, 632
See application file for complete search history.

(56) References Cited

U.S. PATENT DOCUMENTS

| | | | | |
|---|---|---|---|---|
| 3,512,400 A | * | 5/1970 | Lynnworth | 73/597 |
| 4,127,035 A | * | 11/1978 | Vasile | B06B 1/04 73/629 |
| 4,296,486 A | * | 10/1981 | Vasile | H04R 9/047 310/26 |

(Continued)

FOREIGN PATENT DOCUMENTS

| JP | 2004-274597 A | 9/2004 | | |
|---|---|---|---|---|
| JP | 2004274597 A | * | 9/2004 | ............. G01N 29/04 |

(Continued)

OTHER PUBLICATIONS

Search report issued in corresponding application PCT/JP2010/057934, completed Jun. 9, 2010 and mailed Jun. 22, 2010.

*Primary Examiner* — Michael A Lyons
*Assistant Examiner* — Suman K Nath
(74) *Attorney, Agent, or Firm* — Griffin and Szipl PC (57) ABSTRACT

An L-mode guided wave sensor 10 for inspecting an inspection target by using an L-mode guided wave. The L-mode guided wave sensor 10 is provided with a vibrator 3 which is attached to an inspection target 1, and a coil 5 which is wound around the vibrator 3 and to which an AC voltage is applied. The vibrator 3 is made of a ferromagnetic material.

4 Claims, 6 Drawing Sheets

(56) References Cited

U.S. PATENT DOCUMENTS

| | | | | |
|---|---|---|---|---|
| 4,522,071 | A | * | 6/1985 | Thompson ............. G01N 29/07 73/597 |
| 4,604,612 | A | * | 8/1986 | Watkins ................. B64D 15/20 340/582 |
| 8,091,427 | B2 | | 1/2012 | Miki et al. |
| 2004/0095137 | A1 | * | 5/2004 | Kwun ................ G01N 29/2412 324/240 |
| 2009/0031813 | A1 | * | 2/2009 | Miki ...................... G01N 29/07 73/622 |
| 2009/0278651 | A1 | * | 11/2009 | Okada et al. ................. 336/200 |
| 2011/0308316 | A1 | | 12/2011 | Miki et al. |

FOREIGN PATENT DOCUMENTS

| | | |
|---|---|---|
| JP | 4131179 B2 | 8/2008 |
| JP | 2009-36516 A | 2/2009 |

* cited by examiner

FIG. 1

PRIOR ART

L-MODE GUIDED WAVE SENSOR

This is a National Phase Application in the United States of International Patent Application No. PCT/JP2010/057934 filed May 11, 2010, which claims priority on Japanese Patent Application No. 101817/2010, filed Apr. 27, 2010. The entire disclosures of the above patent applications are hereby incorporated by reference.

TECHNICAL FIELD

The present invention relates to an L-mode guided wave sensor which uses a longitudinal mode (L-mode) guided wave to inspect an inspection target. The L-mode guided wave propagates through the inspection target while vibrating in its propagation direction. The frequency of the guided wave is, for example, 1 kHz to several hundred kHz (e.g. 32 kHz, 64 kHz, or 128 kHz).

BACKGROUND ART

Figure 1:
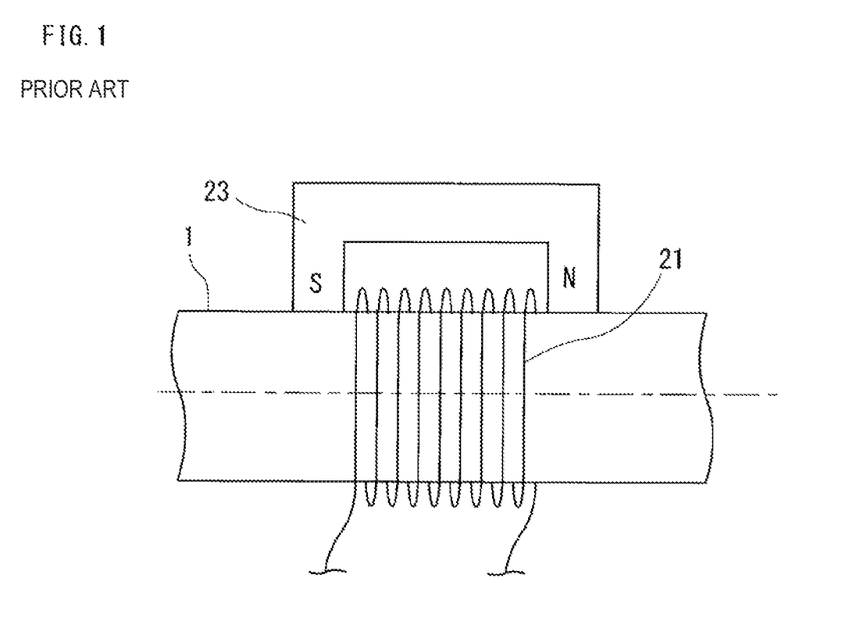
FIG. 1 shows a device conventionally used to generate an L-mode guided wave.

An L-mode guided wave is generated, for example, by a configuration in FIG. 1. In FIG. 1, a coil 21 is wound around an inspection target 1 (pipe in the diagram), and a magnet 23 is attached to the inspection target 1. If an alternating current is passed through the coil 21 in this state, an alternating-current magnetic field is generated. By use of magnetic force resulting from this alternating-current magnetic field and a magnetic field resulting from the magnet 23, the inspection target 1 which is a ferromagnetic body is vibrated by a magnetostrictive effect, and a guided wave which is a kind of a sound wave is thereby generated. The generated guided wave propagates through the inspection target 1 along its longitudinal direction.

A reflected wave of the guided wave is detected to inspect the soundness of the inspection target 1. The guided wave is reflected as a reflected wave by a discontinuous part in the inspection target 1 and by a change in the cross-sectional area of the inspection target 1. By detecting the reflected wave, the soundness of the inspection target 1 is inspected. Regarding the soundness of the inspection target 1, for example, the inspection target 1 is inspected for defects such as a scarred or corroded part.

As compared with a sound wave used in general sound wave inspections, the guided wave attenuates less and enables the soundness of the inspection target 1 to be inspected over a wide range of the inspection target 1. The sound wave used in general sound wave inspections has, for example, a high frequency of 5 MHz and a small wavelength of 0.6 mm, and accordingly easily attenuates. In contrast, the above-mentioned guided wave has, for example, a low frequency of several kHz to several ten kHz and a great wavelength of 100 mm, and accordingly does not easily attenuate.

For example, as prior art of the present application, there is Patent Literature (PTL) 1 specified below.

CITATION LIST

Patent Literature

PTL 1: Japanese Patent Application Laid-open Publication No. 2009-36516

SUMMARY OF INVENTION

Technical Problem

The inspection that uses an L-mode guided wave has the following problems (A) and (B).

(A) A device is increased in size as below. In the configuration in FIG. 1, the coil 21 is wound around the inspection target 1, so that the coil 21 is also increased in dimensions when the inspection target 1 is large. Similarly, when the inspection target 1 is large, there is a need for the large magnet 23 having magnetic force that can hold the magnetic field in the inspection target 1 which is a ferromagnetic body. In this way, the coil 21 and the magnet 23 are increased in dimensions.

(B) In order to generate an L-mode guided wave in the inspection target 1, the inspection target 1 needs to be made of a ferromagnetic material. Accordingly, targets made of materials other than ferromagnetic materials cannot be inspected by an L-mode guided wave.

It is an object of the present invention to provide an L-mode guided wave sensor which can be reduced in size and which can also inspect a target made of a material other than ferromagnetic materials.

Solution to Problem

In order to achieve the foregoing object, the present invention provides an L-mode guided wave sensor that inspects an inspection target by using an L-mode guided wave, the L-mode guided wave sensor comprising: a vibrator which is attached to an inspection target; and a coil which is wound around the vibrator and to which an AC voltage is applied, wherein the vibrator is made of a ferromagnetic material.

According to a preferred embodiment of the present invention, a magnet is attached to the vibrator, and the magnet has a south pole on one side in the axial direction of the coil and has a north pole on the other side in the axial direction of the coil.

Preferably, the vibrator is formed into a thin plate shape.

Advantageous Effects of Invention

According to the present invention described above, the vibrator attached to the inspection target is made of a ferromagnetic material, and the coil is wound around the vibrator, so that the dimensions of the coil does not need to be adjusted to the dimensions of the inspection target. Thus, the L-mode guided wave sensor can be reduced in size.

Moreover, an alternating-current magnetic field generated by the coil is applied to the vibrator which is a ferromagnetic body different from the inspection target, and the vibrator is thereby vibrated. As a result, a guided wave is generated in the inspection target. Accordingly, a target made of a material other than ferromagnetic materials can also be inspected.

DESCRIPTION OF EMBODIMENTS

A preferred embodiment of the present invention will be described with reference to the drawings. The same reference numerals are attached to the common parts in the respective drawings, and the overlapping description will be omitted.

Figure 2A:
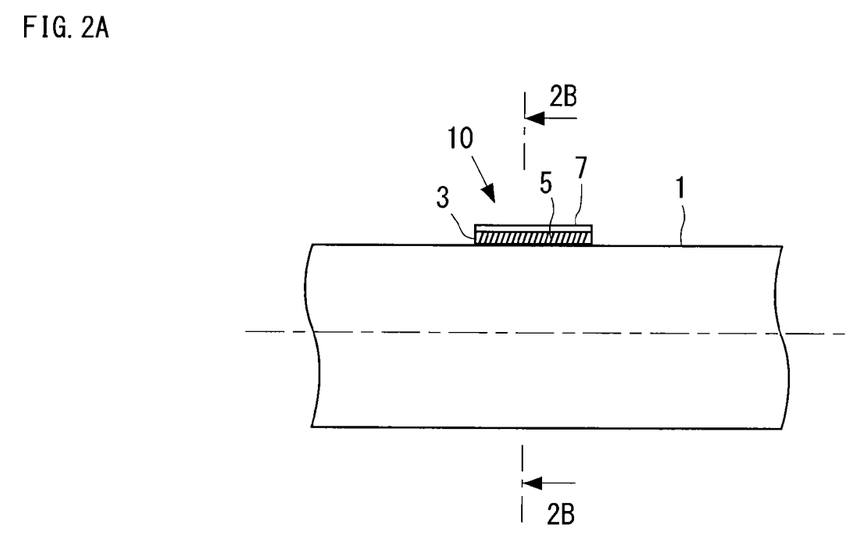
FIG. 2A shows a state where an L-mode guided wave sensor according to an embodiment of the present invention has been attached to an inspection target.
Figure 2B:
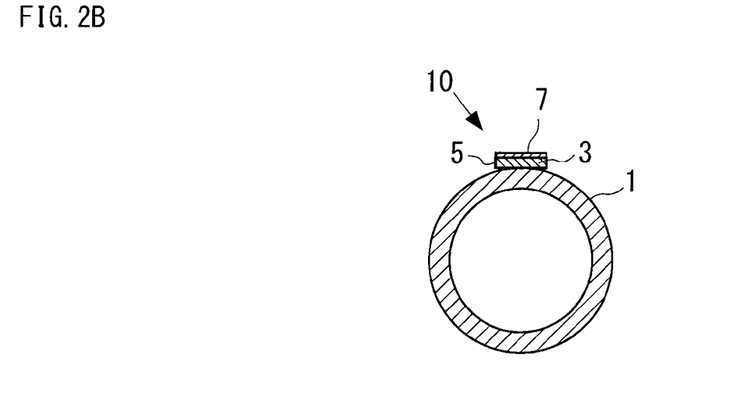
FIG. 2B is a sectional view taken along 2B-2B of FIG. 2A.

FIG. 2A shows a state where an L-mode guided wave sensor 10 according to an embodiment of the present invention is attached to an inspection target. FIG. 2B is a sectional view taken along 2B-2B of FIG. 2A.

Figure 3A:
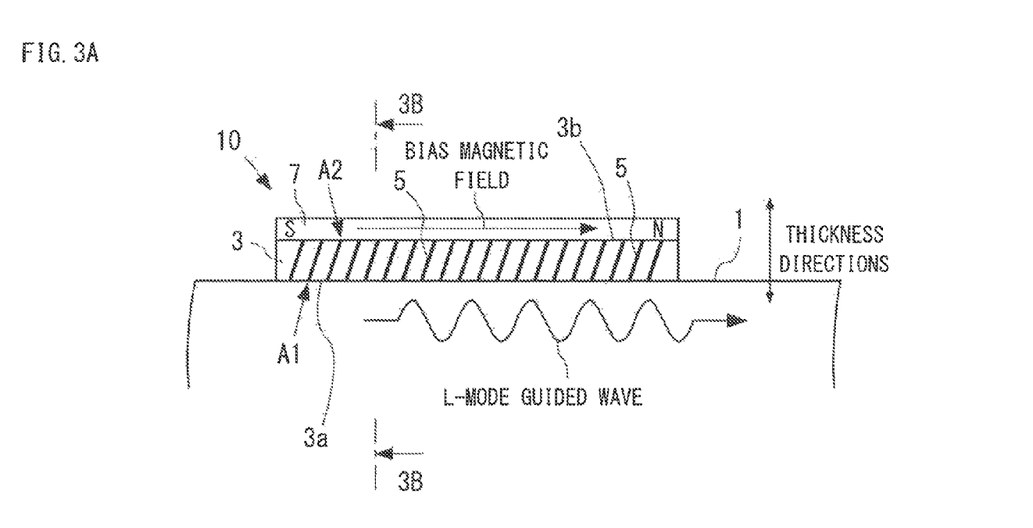
FIG. 3A is a partial enlarged view of a part in the vicinity of the L-mode guided wave sensor in FIG. 2A.
Figure 3B:
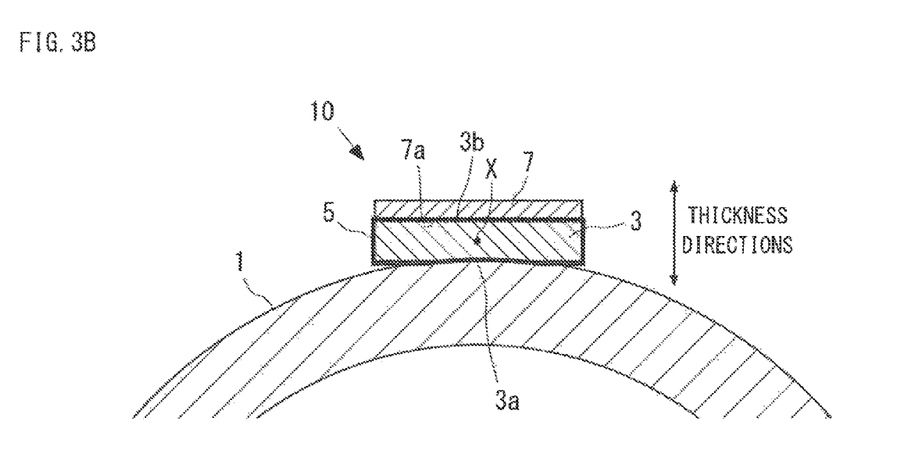
FIG. 3B is a sectional view taken along 3B-3B of FIG. 3A.

FIG. 3A is a partial enlarged view of a part in the vicinity of the L-mode guided wave sensor 10 in FIG. 2A. FIG. 3B is a sectional view taken along 3B-3B of FIG. 3A.

Figure 4A:
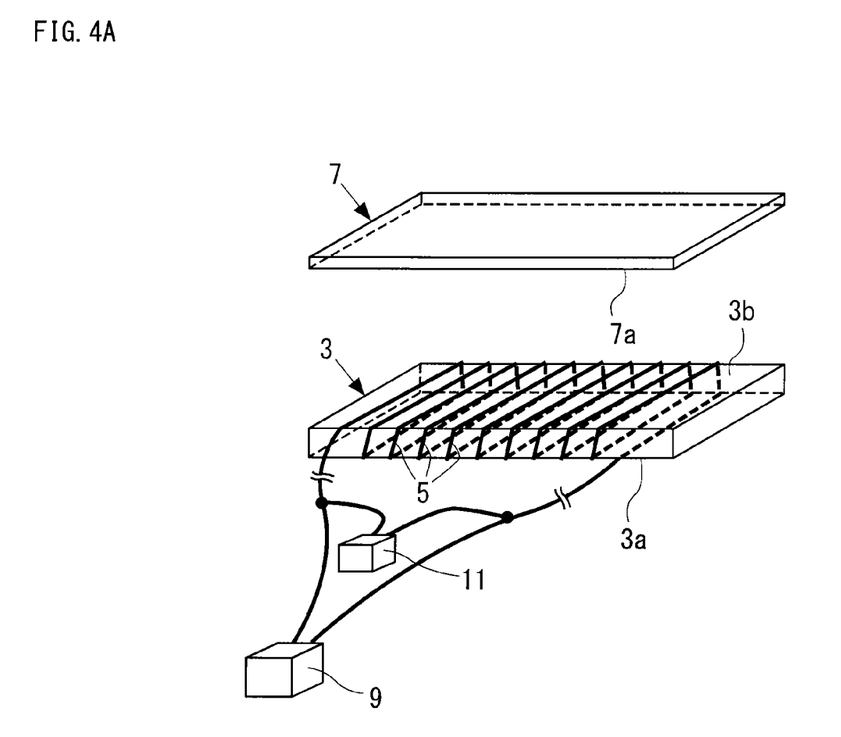
FIG. 4A is a perspective view showing a vibrator and a magnet that are separated in the L-mode guided wave sensor.
Figure 4B:
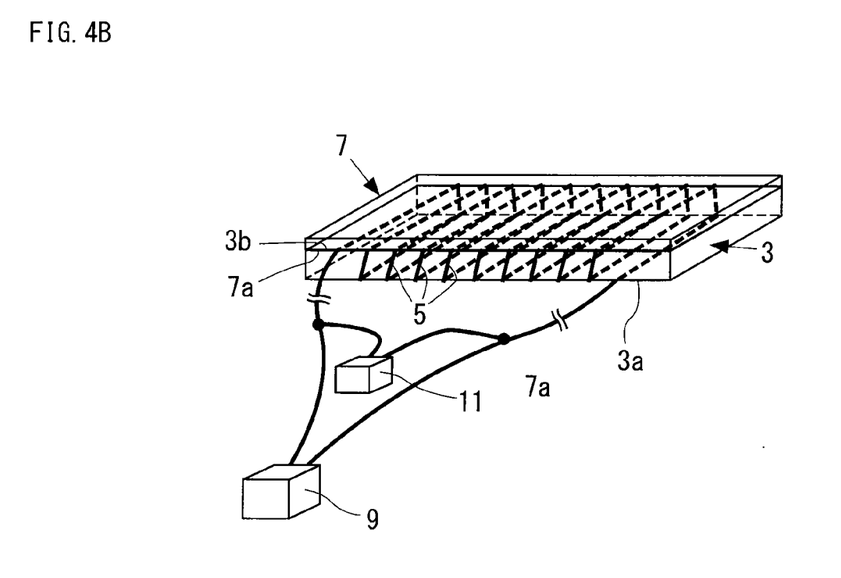
FIG. 4B is a perspective view of the L-mode guided wave sensor.

FIG. 4A is a perspective view showing a vibrator 3 and a magnet 7 that are separated in the L-mode guided wave sensor 10. FIG. 4B is a perspective view of the L-mode guided wave sensor 10.

The L-mode guided wave sensor 10 is a device which uses an L-mode guided wave to inspect the inspection target 1. The L-mode guided wave sensor 10 comprises the vibrator 3, a coil 5, and the magnet 7.

The vibrator 3 is made of a ferromagnetic material. Preferably, as shown in FIGS. 3A and 3B, the vibrator 3 is formed into a thin shape (thin plate shape). As a result, even if the vibrator 3 is small in size, the contact area between the vibrator 3 and the inspection target 1 can be increased so that the vibration of the vibrator 3 may be easily transmitted to the inspection target 1.

A contact surface 3a of the vibrator 3 that contacts the inspection target 1 is a flat surface in the example of FIGS. 3A, 3B, 4A and 4B, but may be a curved surface instead. That is, when the vibrator 3 is formed into a thin shape (thin plate shape), the contact surface 3a of the vibrator 3 may be a curved surface that conforms to the curved shape of the surface of the inspection target 1 to which the contact surface 3a is attached. This permits the whole contact surface 3a of the vibrator 3 to tightly contact with the inspection target 1.

The vibrator 3 may be attached to the inspection target 1 by proper means (a tape or an adhesive agent). However, when the inspection target 1 is made of a magnetic material, the vibrator 3 can be attached to the inspection target 1 by use of the magnetic force of the magnet 7 attached to the vibrator 3.

The coil 5 is wound around the vibrator 3. An AC voltage is applied to the coil 5.

The magnet 7 is attached to the vibrator 3. The magnet 7 has a south pole on one side in the axial direction of the coil 5 and has a north pole on the other side in the axial direction of the coil 5. It is sufficient for the magnet 7 to generate magnetic force that just holds the magnetic field in the ferromagnetic body (vibrator 3). The magnet 7 is preferably a permanent magnet. The magnet 7 is attached to a surface 3b opposite to the contact surface 3a of the vibrator 3.

The magnet 7 is preferably formed into a thin shape (thin plate shape) in the same manner as the vibrator 3. This permits the magnetic field generated by the magnet 7 to efficiently act in the vibrator 3. In this case, an attachment surface 7a of the magnet 7 attached to the surface 3b of the vibrator 3 preferably has a shape that conforms to the shape of the surface 3b of the vibrator 3. This permits the whole attachment surface 7a of the magnet 7 to tightly contact with the vibrator 3.

The vibrator 3, the coil 5, and the magnet 7 are preferably combined together by proper combining means such as an adhesive agent.

As shown in FIGS. 4A and 4B, the L-mode guided wave sensor 10 further comprises an AC power supply 9, and a detector 11. The AC power supply 9 applies an AC voltage to the coil 5. The detector 11 is connected to the coil 5 so as to detect a voltage between both ends of the coil 5. In FIGS. 2A, 2B, 3A and 3B, the AC power supply 9 and the detector 11 are not shown.

As shown in FIGS. 2A, 2B, 3A and 3B, a proper switch is turned on in a state where the vibrator 3 having the coil 5 wound therearound and having the magnet 7 attached thereto is attached to the inspection target 1. Thereby, the AC power supply 9 applies an AC voltage to the coil 5. As a result, the vibrator 3 is vibrated, so that an L-mode guided wave is generated in the inspection target 1, and the guided wave propagates through the inspection target 1. The guided wave thus propagated is reflected by a defective part of the inspection target 1 such as a scarred or corroded part (thickness reduced part), and then return to the position of the vibrator 3. A voltage generated between both ends of the coil 5 when the reflected wave reaches the position of the vibrator 3 is detected by the detector 11.

The following advantageous effects (1) to (7) are obtained by the L-mode guided wave sensor 10 according to the present embodiment described above.

(1) The vibrator 3 attached to the inspection target 1 is made of a ferromagnetic material, and the coil 5 is wound around this vibrator 3, so that the dimensions of the coil 5 does not need to be adjusted to the dimensions of the inspection target 1. Thus, the L-mode guided wave sensor 10 can be considerably reduced in size as compared with FIG. 1.

(2) The vibrator 3 is vibrated by applying an alternating-current magnetic field generated by the coil 5 to the vibrator 3 which is a ferromagnetic body different from the inspection target 1, and a guided wave is thereby generated in the inspection target 1. Accordingly, a target 1 made of materials other than ferromagnetic materials can also be inspected.

(3) The magnetic force of the magnet 7 can be much less than in the prior art, so that the magnet 7 can be reduced in size. The prior art requires a large magnet having magnetic force that can hold the magnetic field in the inspection target 1 which is a ferromagnetic body, as shown in FIG. 1. In contrast, the present embodiment requires the magnet 7 having magnetic force that just holds the magnetic field in the small vibrator 3 (ferromagnetic body). Thus, the magnet 7 can be reduced in size.

(4) The vibrator 3, the coil 5, and the magnet 7 are combined together by proper combining means such as an adhesive agent, so that the vibrator 3, the coil 5, and the magnet 7 become easy to handle. In this case, the vibrator 3, the coil 5, and the magnet 7 that are combined together can serve as the L-mode guided wave sensor 10 in which the coil 5 can be connected to the AC power supply 9 and the detector 11. This L-mode guided wave sensor 10 can be sold as a product separated from the AC power supply 9 and the detector.

(5) As the L-mode guided wave sensor 10 can be reduced in size, it is possible to adapt to various shapes of the inspection targets 1 as follows. Conventionally, the inspection target 1 needs to have a shape (e.g. cylindrical shape) that allows the winding of a coil necessary to generate a guided wave. In contrast, according to the present embodiment, it suffices that the small vibrator 3 is attached to the inspection target 1. For this reason, according to the present invention, a shape of a target 1 to be inspected is not restricted, and targets 1 having various shapes (e.g. a large flat plate) can be inspected.

(6) As the L-mode guided wave sensor 10 can be reduced in size, the L-mode guided wave sensor 10 can be attached to even a narrow portion of the inspection target 1.

Figure 5:
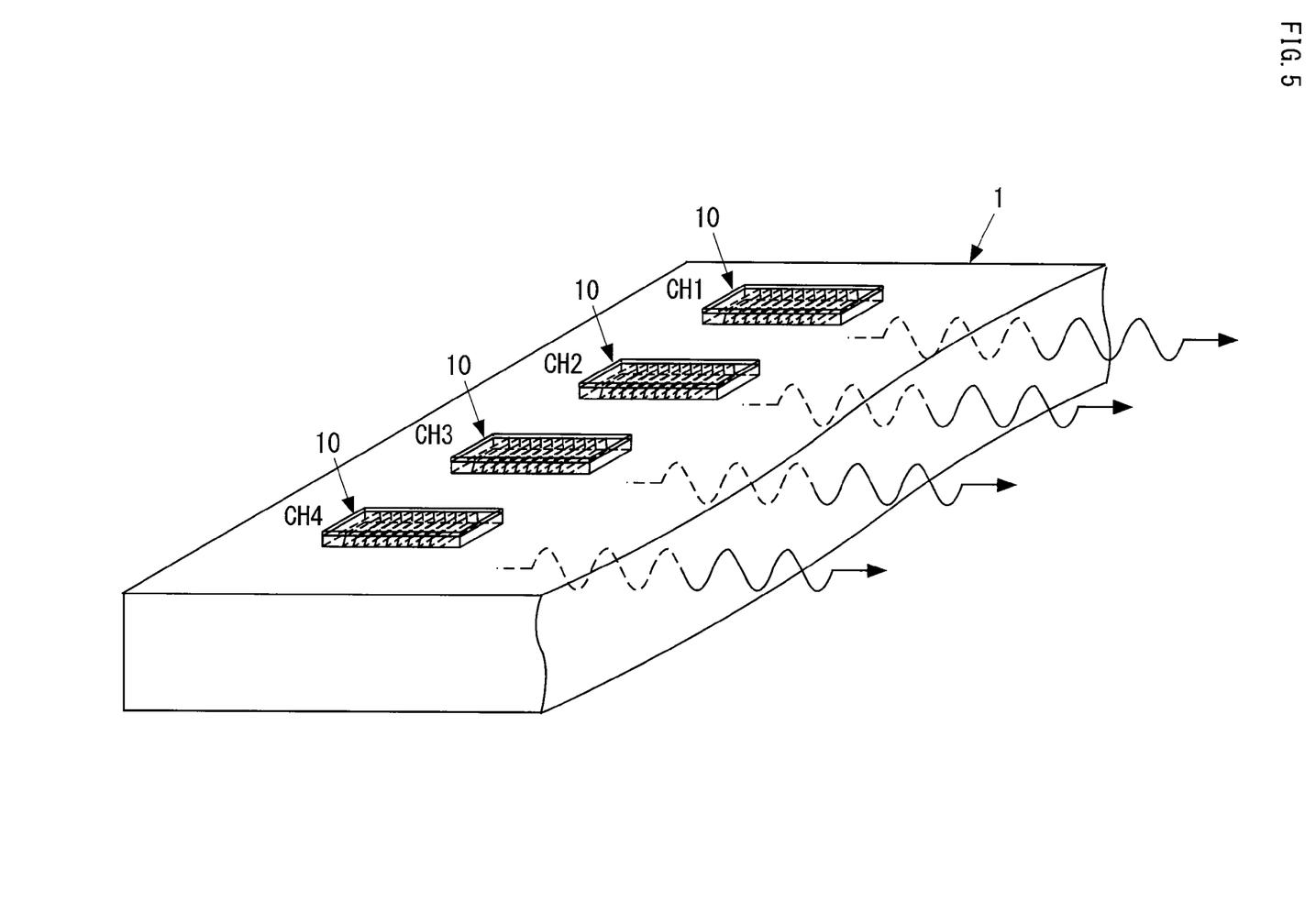
FIG. 5 illustrates multichannel guided waves produced by a plurality of L-mode guided wave sensors.

(7) As the L-mode guided wave sensor 10 can be reduced in size, a plurality of L-mode guided wave sensors 10 can be arranged on the inspection target 1 and attached to the inspection target 1, as shown in FIG. 5. This enables generation of multichannel L-mode guided waves (channels CH1 to CH4 in FIG. 5). In FIG. 5, the AC power supply 9 and the detector 11 of each L-mode guided wave sensor 10 are not shown.

It should be understood that the present invention is not limited to the embodiment described above, and various modifications can be made without departing from the scope of the invention. For example, Modifications 1 to 3 described below may be employed by properly combining any two of or all of Modifications 1 to 3, or any one of Modifications 1 to 3 may be employed.

(Modification 1)

Figure 6A:
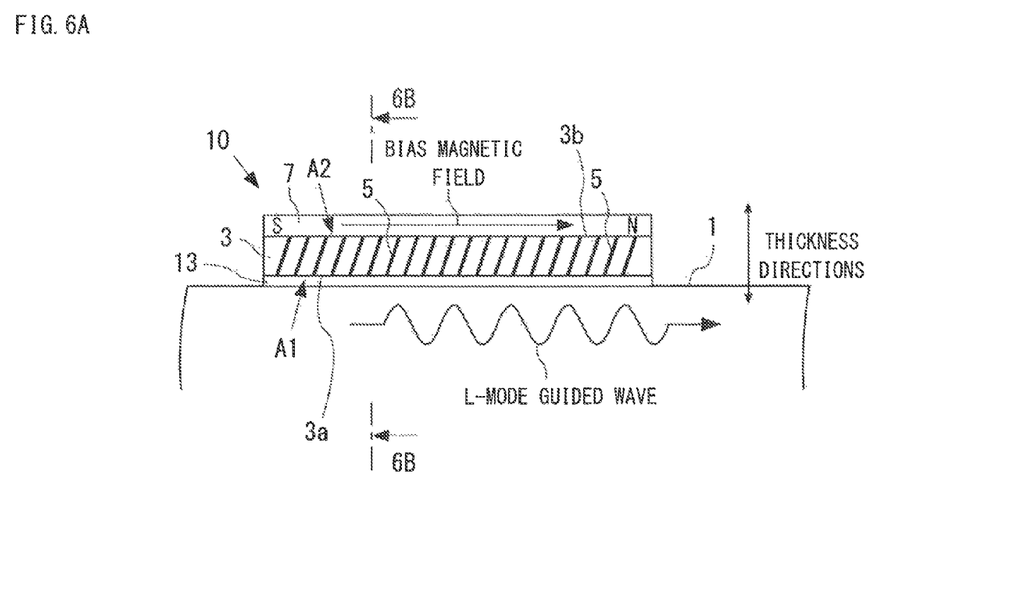
FIG. 6A illustrates a contact medium provided between the vibrator and the inspection target.
Figure 6B:
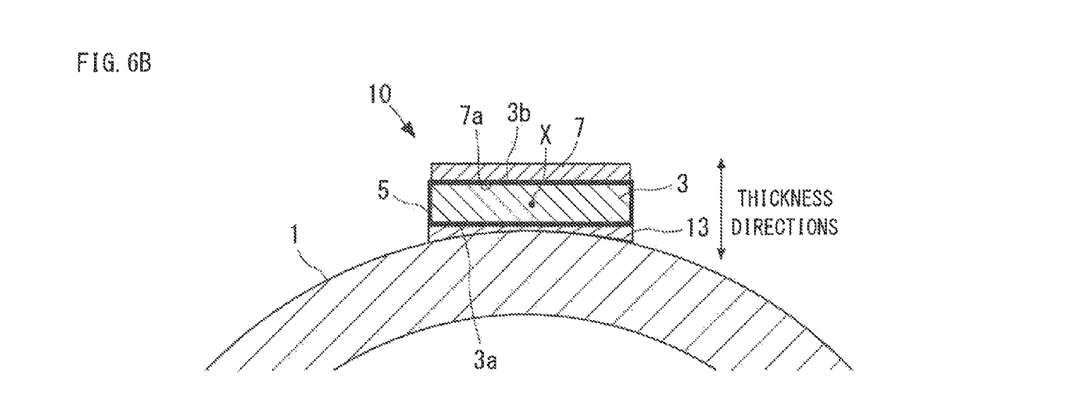
FIG. 6B is a sectional view taken along 6B-6B of FIG. 6A.

Although the vibrator 3 is directly attached to the inspection target 1 in the example of FIGS. 3A and 3B, the vibrator 3 may be attached to the inspection target 1 via a contact medium 13, as shown in FIGS. 6A and 6B. FIG. 6A corresponds to FIG. 3A, and shows a case in which the contact medium 13 is provided. FIG. 6B is a sectional view taken along 6B-6B of FIG. 6A.

Even if a large contact area cannot be secured between the vibrator 3 and the inspection target 1, the contact medium 13 improves vibration transmission between the vibrator 3 and the inspection target 1. The contact medium 13 may be a deformable solid such as an adhesive agent or a tape that combines the vibrator 3 and the inspection target 1, or may be liquid that fills a space between the vibrator 3 and the inspection target 1. When a solid is used as the contact medium 13, the contact medium 13 preferably has a shape that can tightly contact with both of the vibrator 3 and the inspection target 1. When liquid is used as the contact medium 13, the liquid is preferably held in the space between the vibrator 3 and the inspection target 1 by proper means (e.g. a sealing material bonded to the inspection target 1 around the space).

(Modification 2)

The magnet 7 may be an electromagnet instead of the permanent magnet. In this case, the magnet 7 comprises a solid portion (preferably, a core portion made of a magnetic material), and a coil wound around the solid portion. A DC current is passed through the coil so that the magnetic field acts on the vibrator 3.

(Modification 3)

The magnet 7 may be omitted. That is, the magnetic field generated in the ferromagnetic vibrator 3 by applying an AC voltage to the coil 5 can cause an L-mode guided wave to propagate through the inspection target 1. In this case, the magnet 7 may be omitted, and the other points are the same as the above description.

REFERENCE SIGNS LIST

1: inspection target; 3: vibrator; 3a: contact surface (first side surface) of the vibrator; 3b: surface (second side surface) opposite to the contact surface; 5: coil; 7: magnet; 9: AC power supply; 10: L-mode guided wave sensor; 11: detector; 13: contact medium; A1: an area on a side of the first side surface; A2: an area on a side of the second side surface; and X: axis of the coil (5).

The invention claimed is:

1. An L-mode guided wave sensor that inspects an inspection target by using an L-mode guided wave, comprising:
   a vibrator which during normal use is attached to an inspection target; and
   a coil to which an AC voltage is applied,
   wherein the vibrator is formed into a plate shape by a ferromagnetic material,
   the vibrator includes a first side surface and a second side surface,
   the first side surface and the second side surface are respectively located on sides opposite to each other in thickness directions of the vibrator,
   the first side surface faces an outer surface of the inspection target during normal use,
   the coil is wound around the vibrator such that an axis of the coil extends in a direction perpendicular to the thickness directions, and the coil repeatedly and alternately passes an area on a side of the first side surface and an area on a side of the second side surface, and
   in a state where the vibrator is attached to the outer surface of the inspection target such that the first side surface of the vibrator faces the outer surface of the inspection target, the AC voltage is applied to the coil, so that vibration of the vibrator is transmitted to the inspection target to generate an L-mode guided wave in the inspection target.

2. The L-mode guided wave sensor according to claim 1, wherein a magnet is attached to the vibrator, and
   the magnet has a south pole and a north pole that are respectively on sides opposite to each other in an axial direction of the coil.

3. A method of using an L-mode guided wave sensor, the method comprising the steps of:
   providing the L-mode guided wave sensor, wherein the L-mode guided wave sensor comprises a vibrator and a coil, wherein the vibrator is formed into a plate shape by a ferromagnetic material, the vibrator includes a first side surface and a second side surface, the first side surface and the second side surface are respectively located on sides opposite to each other in thickness directions of the vibrator, the coil is wound around the vibrator such that an axis of the coil extends in a direction perpendicular to the thickness directions, and the coil repeatedly and alternately passes an area on a side of the first side surface and an area on a side of the second side surface;
   attaching the vibrator to an outer surface of an inspection target such that the first side surface of the vibrator faces the outer surface of the inspection target; and
   in a state where the vibrator is attached to the outer surface of the inspection target, applying an AC voltage to the coil, so that vibration of the vibrator is transmitted to the inspection target to generate an L-mode guided wave in the inspection target.

4. A method of using an L-mode guided wave sensor, the method comprising the steps of:
   providing the L-mode guided wave sensor, wherein the L-mode guided wave sensor comprises a vibrator and a coil, wherein the vibrator is formed into a plate shape by a ferromagnetic material, the vibrator includes a first side surface and a second side surface, the first side surface and the second side surface are respectively located on sides opposite to each other in thickness directions of the vibrator, the coil is wound around the vibrator such that an axis of the coil extends in a direction perpendicular to the thickness directions, the coil repeatedly and alternately passes an area on a side of the first side surface and an area on a side of the second side surface, a magnet is attached to the vibrator, and the magnet has a south pole and a north pole that are respectively on sides opposite to each other in an axial direction of the coil;

attaching the vibrator to an outer surface of the inspection target such that the first side surface of the vibrator faces the outer surface of the inspection target, and in a state where the vibrator is attached to the outer surface of the inspection target, applying an AC voltage to the coil, so that vibration of the vibrator is transmitted to the inspection target to generate an L-mode guided wave in the inspection target.

\* \* \* \* \*